United States Patent [19]
Mehra

[11] 4,421,535
[45] Dec. 20, 1983

[54] PROCESS FOR RECOVERY OF NATURAL GAS LIQUIDS FROM A SWEETENED NATURAL GAS STREAM

[75] Inventor: Yuv R. Mehra, Odessa, Tex.

[73] Assignee: El Paso Hydrocarbons Company, Odessa, Tex.

[21] Appl. No.: 374,270

[22] Filed: May 3, 1982

[51] Int. Cl.³ ............................................. F25J 1/02
[52] U.S. Cl. ......................................... 62/17; 62/23
[58] Field of Search ................. 62/17, 20, 23, 9, 11; 55/68, 73, 76

[56] References Cited

U.S. PATENT DOCUMENTS 4,252,548  2/1981  Markbreiter et al. ................. 62/17

Primary Examiner—Frank Sever
Attorney, Agent, or Firm—Depaoli & O'Brien

[57] ABSTRACT

A sweet natural gas stream is stripped of water and hydrocarbon components heavier than methane to substantially any selected degree by countercurrent extraction with polyethylene glycol dimethyl ether while at pipeline pressures. The stripped natural gas meets pipeline specifications. The rich polyethylene glycol dimethyl ether is let down in pressure through selected successive stages which respectively isolate fractions that are rich in ethane, propane, butanes, and hydrocarbons heavier than butane. Lastly, waste water is removed from the solvent to regenerate the polyethylene glycol dimethyl ether. The separated gas streams of ethane, propane, butanes, and hydrocarbons heavier than butanes are individually compressed, combined, condensed and cooled to form a natural gas liquid stream, suitable for pipeline shipment. A sour natural gas stream may also be treated in the same equipment if adequate solvent quantities are employed to remove water and acidic components from the sour gas and if a sweetening unit is added to remove the acidic components from the combined liquid hydrocarbon stream.

25 Claims, 4 Drawing Figures

PROCESS FOR RECOVERY OF NATURAL GAS LIQUIDS FROM A SWEETENED NATURAL GAS STREAM

BACKGROUND OF THE INVENTION

1. Field of the Invention

This invention relates to the treatment of hydrocarbons and more specifically relates to separating and recovering ethane and higher boiling hydrocarbons from the methane in a natural gas stream which has been sweetened by removal of acidic components, such as $CO_2$, $H_2S$, RSH, RSSR, and ammonia.

2. Review of the Prior Art

Raw natural gas as it originates from subterranean reservoirs, either out of solution from crude oil or unassociated with crude oil, can be classified as rich natural gas, rich gas, or lean natural gas. These terms are relative.

Rich natural gas contains a mixture of individual gaseous constituents, some of which can be liquified at atmospheric temperatures and pressures when isolated. The quantities of each component vary from one gas to another, with methane as a usual majority component. Other hydrocarbon components include ethane, propane, isobutane, normal butane, isopentane, normal pentane, hexane, heptane, octane, and nonane, in the order of increasing molecular weight and increasing boiling temperature. Usually, natural gases contain some gaseous contaminations such as nitrogen, carbon dioxide, carbonyl sulfide, hydrogen sulfide, mercaptans, disulfides, ammonia, and water. However, all of these impurities except water and nitrogen are removed by sweetening. Such a sweet natural gas stream is the subject of this invention.

"Lean natural gas" is a term applied to a natural gas which consists of only the lower molecular weight gaseous components, consisting for the most part of methane with variant quantities of ethane, propane, and only very small traces of higher molecular weight components, if any. Such a lean natural gas can occur naturally but generally results from processing a rich natural gas in accordance with recognized industrial methods.

Such a lean natural gas stream, if it contains a high proportion of ethane and propane, may be treated according to the method of this invention to produce desired quantities of these hydrocarbons.

The sweet natural gas stream which is preferably handled according to the method of this invention contains nitrogen, methane, ethane, propane, iso and normal butanes, iso and normal pentanes, hexane, heavier hydrocarbon components, and water. However, there are no acid gases or other acidic impurities, such as $CO_2$, COS, $H_2S$, RSH, RSSR, and ammonia, unless a terminal treatment step is added to the process.

If a natural gas is mostly methane with minor concentrations of ethane, propane, and butanes, it is called a "dry gas", meaning that it has a very low hydrocarbon dew point. The larger the quantity of heavier hydrocarbons such as pentane and higher homologs, e.g., to $C_{18}$, the higher is the hydrocarbon dew point. Frequently, the heavier hydrocarbons are present in sufficient quantities to justify passing the gas through a "gasoline extraction plant" which removes ethane and propane in addition to the heavier hydrocarbons. In some instances, the hydrocarbon dew point is high enough to require a "dew point control station" which removes enough of the heavy hydrocarbons to lower the dew point sufficiently to permit pipeline transmission but does not remove as much of the heavier materials, in addition to the large percentage of the propane and ethane, as is removed by a gasoline extraction plant. Furthermore, the gas coming from the wellhead is usually saturated with water which must be largely removed in order to prevent the formation of ice and hydrates or the accumulation of water which can block the flow and cause corrosion.

Numerous processes have been used to extract liquids from natural gas streams. These processes include oil absorption, refrigerated oil absorption, simple refrigeration, cascaded refrigeration, Joule-Thompson expansion, cryogenic turbo-expansion, and absorption by oxygen-containing liquids.

Oil absorption processes, such as that described in U.S. Pat. No. 2,428,521, are the original separation processes and commonly recover butanes plus heavier components, with some amounts of propane, from natural gas streams. Refrigerated oil absorption processes are similar to the absorption processes except that the oil is cooled by external refrigeration before absorption of liquid components from the gas streams. The recoveries of propane plus components are improved by cooling the absorption oil. Plants using these processes are extremely complex and energy extensive.

A simple refrigeration process includes cooling the gas directly with a single refrigerant, such as propane. Condensed liquids are separated from the gas and are pumped to product pipelines. The recoveries of a simple refrigeration system are better than those of oil absorption units. A cascaded refrigeration process includes several levels of refrigeration, using at least two refrigerants, such as ethane refrigerant cascaded into a propane refrigerant cycle. The recoveries of cascade refrigeration systems are quite good, but units using these processes are not very economical because of high operating and installing costs.

The Joule-Thompson process is a step forward because it uses the refrigeration from the components of a natural gas stream by letting down its pressure. When the residue gas is required at essentially the same pressure as the inlet gas, however, this process becomes quite expensive. A cryogenic expander process has less energy consumption than a Joule-Thompson process for a given recovery, primarily because a portion of the total recompression of residue gas is provided by the turbo-expander. The Joule-Thompson and cryogenic expander processes are primarily used when ethane is to be extracted from natural gas streams. These processes can achieve ethane recoveries as high as 85% to 90%.

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is quite poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80-85%), but recompression of most of the inlet gas is quite expensive.

Under poor economic conditions when the liquid ethane price as petrochemical feedstock is less than its equivalent fuel price and when the propane price for feedstock usage is attractive, the operator of a natural gas liquid extraction plant would prefer to maximize the propane recovery while minimizing the ethane recovery but is limited in operating choice. The refrigeration process, which typically recovers 80% of the propane, requires the recovery of typically 35% of the ethane in the inlet gas. In order to boost propane recovery to the 95+% level, cascaded refrigeration, Joule-Thompson, cryogenic, and turbo-expander processes would be required simultaneously to boost the ethane recovery to 70+% at a considerably larger capital investment.

Absorption processes are available that employ liquids other than hydrocarbon oils for removal of acidic components including $H_2S$ and $CO_2$, water, and heavier hydrocarbons which are lost. These liquids comprise propylene carbonate, N-methyl pyrrolidone, glycerol triacetate, polyethyleneglycol dimethyl ether, triethylolamine, tributyl phosphate, and gamma butyrolactone. In particular, U.S. Pat. No. 3,362,133 is directed to sour natural gas mixtures containing $H_2S$ and $CO_2$ and teaches the selection of any dialkyl ether of a polyalkylene glycol as the ether component of a solvent for withdrawing $H_2S$. A mixture of six dimethyl ethers of polyethylene glycol (DMPEG) is said to be effective. The solvent/gas ratio is 0.1 to 1.8 pounds of solvent per standard cubit foot (scf) of $H_2S$ to be absorbed because less than this amount will not effectively remove $H_2S$ and larger amounts of $CO_2$. The $H_2S$-rich and $CO_2$-rich DMPEG solvent is flashed at 15–500 psi lower pressure than in the absorber (preferably, 65 psi lower pressure) in a flash tank which produces gas having substantially all of the $CO_2$ and one-fourth of the $H_2S$. This gas is returned to the absorber. The DMPEG solvent is heated, reduced in pressure, and passed through a packed column as air is passed upwardly. The solvent must contain no more than 0.001% $H_2S$ when it returns to the absorber. The $CO_2$ and $H_2S$ which are vented from the top of the stripping column contain dissolved hydrocarbons which represent a significant loss.

U.S. Pat. No. 3,770,622 relates to treatment for natural gas to remove three troublesome components: $CO_2$, $H_2S$, and hydrocarbons heavier than methane. The preferred solvent is propylene carbonate. Polyethylene glycol dimethyl ether may be passed in counter-flowing contact with a natural gas mixture to remove $CO_2$ and-/or $H_2S$ acid gases plus $C_2$–$C_{18}$ hydrocarbon components from methane gas streams. $CO_2$, $H_2S$, and light hydrocarbons are partially separated from the solvent by flashing. Liquid hydrocarbons, $C_4$ and heavier, having gasoline value are then separated in a settler from liquid solvent and from a vaporphase mixture of $C_2$–$C_{12}$ hydrocarbon vapor, $H_2S$, and/or $CO_2$. In the Example, the three flash streams together contain 43.76% of $C_2$–$C_{12}$ hydrocarbons which represent a signficant loss of desirable hydrocarbons with the $CO_2$ and $H_2S$ vent gases.

U.S. Pat. No. 3,837,143 describes simultaneous dehydration and sweetening of natural gas to produce therefrom a purified natural gas having a low dew point and a low sulfur content by using a normally liquid dialkylether of a polyalkylene glycol ether containing 2–15% water by weight in direct contact with the natural gas. In this process, the natural gas is significantly dry with respect to $C_2+$ hydrocarbons. Example 1 illustrates a loss of 74% of $C_2+$ hydrocarbons with the $CO_2$ and $H_2S$ vent stream while Example 2 shows a loss of 11.6% for $C_2+$ hydrocarbons. These losses, when applied to a wet natural gas stream, indicate a significant economic penalty for sweetening wet gases with DMPEG.

U.S. Pat. No. 4,052,176 relates to a synthesis gas and teaches further purification thereof with dimethyl ether of polyethylene glycol to absorb remaining $CO_2$, $H_2S$, and COS. In this process DMPEG is used to treat a stream that does not contain $C_2+$ hydrocarbons.

U.S. Pat. No. 4,070,165 teaches sweetening a raw natural gas by countercurrent contact with a lean amine solution, dehydrating by contact with a dry glycol stream, and removal of heavier hydrocarbons (after depressurizing) by scrubbing with a lean hydrocarbon stream which is then fractionated to produce methane, ethane, and propane. Dimethyl ether of polyethylene glycol is mentioned as useful for both water and $H_2S$ removal. The natural gases which are suitable for liquefaction and which exist at pressures higher than 800 psig are usually dry and contain few $C_2+$ heavier hydrocarbons. This patent also teaches the preference of amines over DMPEG for removing the $H_2S$ and $CO_2$ contents of the raw natural gas stream in order to eliminate hydrocarbon losses with $CO_2$ and $H_2S$ vent streams.

As presented at the 59th Annual Gas Processor's Association Convention, Mar. 17–19, 1980, in a paper entitled "High $CO_2$-High $H_2S$ Removal With SELEXOL Solvent" by John W. Sweny, the relative solubility in DMPEG of $CO_2$ over methane is 15.0 while that of propane is 15.3. The relative solubility of $H_2S$ over methane is 134 in DMPEG vs. 83 for normal pentane in DMPEG. The relative solubilities in DMPEG of iso and normal butanes and iso pentanes are in between those of propane and $H_2S$. Such data indicate that if $CO_2$ and $H_2S$ are present in a natural gas stream which contains $C_2+$ heavier hydrocarbons which are desirable for petrochemical industry feedstocks, substantial quantities of $C_2+$ hydrocarbons will be lost with $CO_2$ and $H_2S$ vent streams when the natural gas is treated with DMPEG.

Sweet natural gas is usually saturated with water at its ambient temperature which may have a range of 75°–120° F., so that its water content may vary from 20 pounds to more than 50 pounds per million standard cubic feet. However, difficulties are frequently met while pumping such natural gas unless the water content is reduced to a value of less than 12 pounds, preferably less than 7 pounds, of water per million standard cubic feet of natural gas. In terms of dew point, a natural gas having a dew point of 30° F., preferably 20° F. or lower, is generally considered safe for transportation in a pipeline. Dehydration can be carried out under a wide range of pressures from 15 to 5000 psig, but it is usually carried out at pipeline pressures of 500–1500 psig and generally near 1000 psig.

There is nevertheless a need for a process wherein ethane and heavier hydrocarbons and water can be simultaneously removed to a selected degree from methane contained in a sweet natural gas stream without inclusion of steps involving drying thereof. There is further a need for a process wherein propane and heavier hydrocarbons can be extracted from a sweet natural gas stream without the need to extract significant quantities of ethane. There is further a need for a process wherein any natural gas, from very sour to entirely sweet, can be handled by the same equipment while simultaneously dehydrating the gas and recovering the heavier hydrocarbons.

SUMMARY OF THE INVENTION

The object of this invention is to provide an absorption process for removing ethane plus heavier hydrocarbon components from a sweet natural gas stream by contact with an alkyl ether of polyethylene or polypropylene glycol or mixtures thereof according to an extremely flexible wide range of ethane recoveries without requiring additional equipment therefor.

An additional object is to provide a process for removing $C_3+$ components from a sweet natural gas stream by contact with the same solvent without requiring the recovery of ethane from this natural gas stream and while keeping high recovery levels for $C_3+$ components.

Another object is to provide a process for removing $C_2+$ components, water, and acid components from a sour natural gas stream by contact with the same solvent and to separate all such components from the solvent and in the same equipment and then to separate the acid components from the $C_2+$ components.

In accordance with these objects, the process of this invention uses dimethylether of polyethylene glycol for extracting ethane and heavier hydrocarbon components and water, if present, from a sweet natural gas stream, at any desired ethane recovery from 2% to 98%. The inlet gas pressure can range from 300 psig to 1300 psig and from an ambient temperature of 80° F. to 120° F.

It is well know that the ratio of ethane to methane can be varied at will by changing the flowrate of the solvent. The absorption principle leads to an alpha or relative volatility between methane and ethane of slightly less than 5 for almost all known absorption oils. However, the relative volatility between methane and ethane in the presence of dimethyl ehter of polyethylene glycol (DMPEG) is 6.4, indicating that it is more selective toward ethane than other absorption oils. N-methyl pyrollidone (NMP) and dimethyl formamide (DMF) have relative volatilities between methane and ethane of 5.3 and 8.5, respectively. However, the solubility of hydrocarbons in NMP is 0.03 standard cubic feet per gallon (SCF/gal) and in DMF of 0.04 SCF/gal; these are low when compared to 1.0 SCF/gal for DMPEG. Therefore, it is the combination of improved selectivity towards ethane and the hydrocarbon loading capacity of dimethyl ether of polyethylene glycol that makes it a superior absorption solvent for separating and recovering the components of a sweetened natural gas stream that are heavier than methane.

The most suitable range of molecular weight for dimethyl ether of polyethylene glycol is 146 to 476, containing 3-10 ethylene units. The glycol can be branched, such as polypropylene glycol. The basic difference between the behaviors of ethyl and propyl groups is the affinity for water for the ethyl and greater affinity for hydrocarbons for the propyl group. A mixture of dimethyl ethers of polyethylene and polypropylene glycol in various combinations is consequently suitable for recovering ethane plus heavier hydrocarbons from a natural gas. In such a mixture, the content of alkyl ether of polyethylene glycol should be a minimum of 20% by volume, with alkyl ether of polypropylene glycol being limited to 80% by volume maximum.

According to this process, the inlet gas enters the extractor at the bottom and flows upward while dimethyl ether of polyethylene glycol, as solvent, enters the extractor near the top and flows downward. The gas and liquid solvent contact one another in any suitable liquid-gas contacting means, such as distillation trays or column packing. The quantity of liquid solvent that is useful is a function of contact area, inlet gas flow rate, gas pressure, and/or design recoveries of ethane plus heavier hydrocarbon components.

The gas leaving overhead from the extractor meets pipeline specifications. The liquid solvent, rich in ethane plus heavier hydrocarbon components, is let down in pressure in stages in order to reduce energy consumption. In all embodiments described hereinafter, the first stage is represented by a medium-pressure flash tank wherein some of the methane is flashed and then compressed. The liquid solvent, containing ethane plus heavier hydrocarbon components, is further let down to a lower-pressure flash tank wherein more of the ethane, propane and some butanes are flashed. These are also compressed.

In some embodiments, the liquids from the low-pressure flash tank are again let down to an atmospheric-pressure flash tank, where all the remaining hydrocarbons which are absorbed in the extractor are flashed out of the solvent and compressed, or, in one preferred embodiment, are let down directly to a vacuum flash tank where the remaining hydrocarbons are also flashed out of the solvent. Where an atmospheric flash tank is utilized, a vacuum flash tank may be selectively installed thereafter. A demethanizer column may advantageously be utilized after the vacuum flash tank.

If the inlet gas stream to the extractor contains water, the liquid in the atmospheric flash tank is composed of dimethyl ether of polyethylene glycol and water, since the relative solubility in DMPEG of water to methane is 11000 as compared to the similar relative solubility for normal heptane of 360. In order to remove this water, the liquid is pumped from the atmospheric flash tank to a solvent regenerator, wherein water is separated overhead while the pure solvent is pumped for recycling back to the extractor. Depending upon the water content of the sweet inlet gas being fed to the extractor, water may be stripped from the solvent with the help of a stripping gas such as dry compressed air, nitrogen, or methane. Alternatively, a reboiler may be required if such stripping gas is not available. If the inlet sweet gas does not contain any water, the solvent regenerator can be bypassed by recycling the pure solvent from the atmospheric flash tank to the extractor.

The gases leaving the medium-pressure and low-pressure flash tanks, after compression and cooling, are generally returned to the extractor. The gases leaving the atmospheric and vacuum flash tanks are suitably combined, if both flash tanks are used, compressed and condensed in a cooler and then stored in a storage vessel as liquids. From this vessel, the liquids are pumped to a pipeline. The off-gas from the demethanizer is compressed, cooled, and returned to the extractor.

In general, the smaller the quantity of $C_5+$ hydrocarbons in the natural gas stream, the higher the final flashing pressure can be. The range of pressures that are needed in a vacuum tank is in the range of 2 to 25 psia. The quantity of $C_2+$ hydrocarbons also affects the amount of methane that is picked up by the solvent and removed in the demethanizer. In general, the richer the feed in $C_2+$ hydrocarbons, the less the methane pickup will be. Consequently, when treating a very rich feed, a demethanizer is likely not to be needed.

$CO_2$ and $H_2S$ have solubilities in DMPEG that are very close to the solubilities of propane and pentane, respectively in this solvent. Therefore it is difficult to separate these acidic materials from the desirable gases when treating sour natural gas, and the prior art has tended to perform this separation before removing hydrocarbons, thereby requiring large capacity equipment and losing significant quantities of desirable hydrocarbons with $CO_2$ and $H_2S$ vent streams. Widespread usage of DMPEG has obviously been avoided. In one of the embodiments of this invention, $CO_2$ and $H_2S$ are allowed to remain with the desirable gases until final stages in the process where they are removed as liquids requiring smaller and less expensive equipment.

This treatment procedure requires the usage of substantially larger quantities of DMPEG than has been recommended by the prior art. There is, consequently, enough absorption capacity in the DMPEG stream when equilibrium is reached that the acidic materials in the recycle stream and in the sour natural gas can be completely removed, thereby producing a sweet methane-rich stream from the top of the extractor, meeting pipeline specifications. The advantage of this treatment method over those of the prior art is that a single plant can accept a very wide variety of natural gas streams, from very acidic to completely sweet, simply by utilizing the acid removal unit (e.g., an amines process) to a selective extent or even by by-passing it entirely.

The advantages of this invention are as follows:
1. low capital investment;
2. low energy and operating costs;
3. low maintenance requirements;
4. no special metallurgical requirements;
5. reduced environmental emissions;
6. simple in operation, even permitting unattended operation;
7. operable in remote locations where water is not available;
8. no freeze up problems caused by cold temperature;
9. optimum operation at essentially ambient temperature so that minimal to no insulation is required;
10. minimum heat exchange needed, so that no fouling of equipment occurs;
11. suitable operation at pipeline pressure even during pressure swings;
12. no need for catalyst, chemicals, inhibitors, or additives;
13. minimal to no need for refrigeration;
14. extremely flexible, wide range of ethane recoveries without additional equipment, based on market economics, such recoveries varying from as high as 98% to as low as 2%, i.e., operation can vary from ethane recovery to ethane rejection;
15. solvent is non-toxic, biodegradable, and environmentally acceptable;
16. solvent is non-corrosive, non-foaming, non-degrading, and hygroscopic;
17. solvent has extremely low vapor pressure, e.g., 0.002 mm Hg at 77° F., resulting in minimum solvent losses;
18. solvent does not require mixing with any other base, so that no compositions need be maintained for extraction of liquid hydrocarbon;
19. solvent has high loading capacity, thereby minimizing its circulation rate;
20. dry or water-saturated inlet gas streams can be processed;
21. operation is continuous, with no cycling of drier beds for drying and regeneration, and
22. no need to dry the gas to 1 ppm $H_2O$ because no cryogen is required in the process.

BRIEF DESCRIPTION OF THE DRAWINGS

The invention may be more readily understood by referring to the drawings which diagrammatically illustrate preferred embodiments for treating both sweet and sour natural gases for removal of water and hydrocarbons heavier than methane from a wellhead natural gas stream.

DESCRIPTION OF THE PREFERRED EMBODIMENTS

Figure 1:
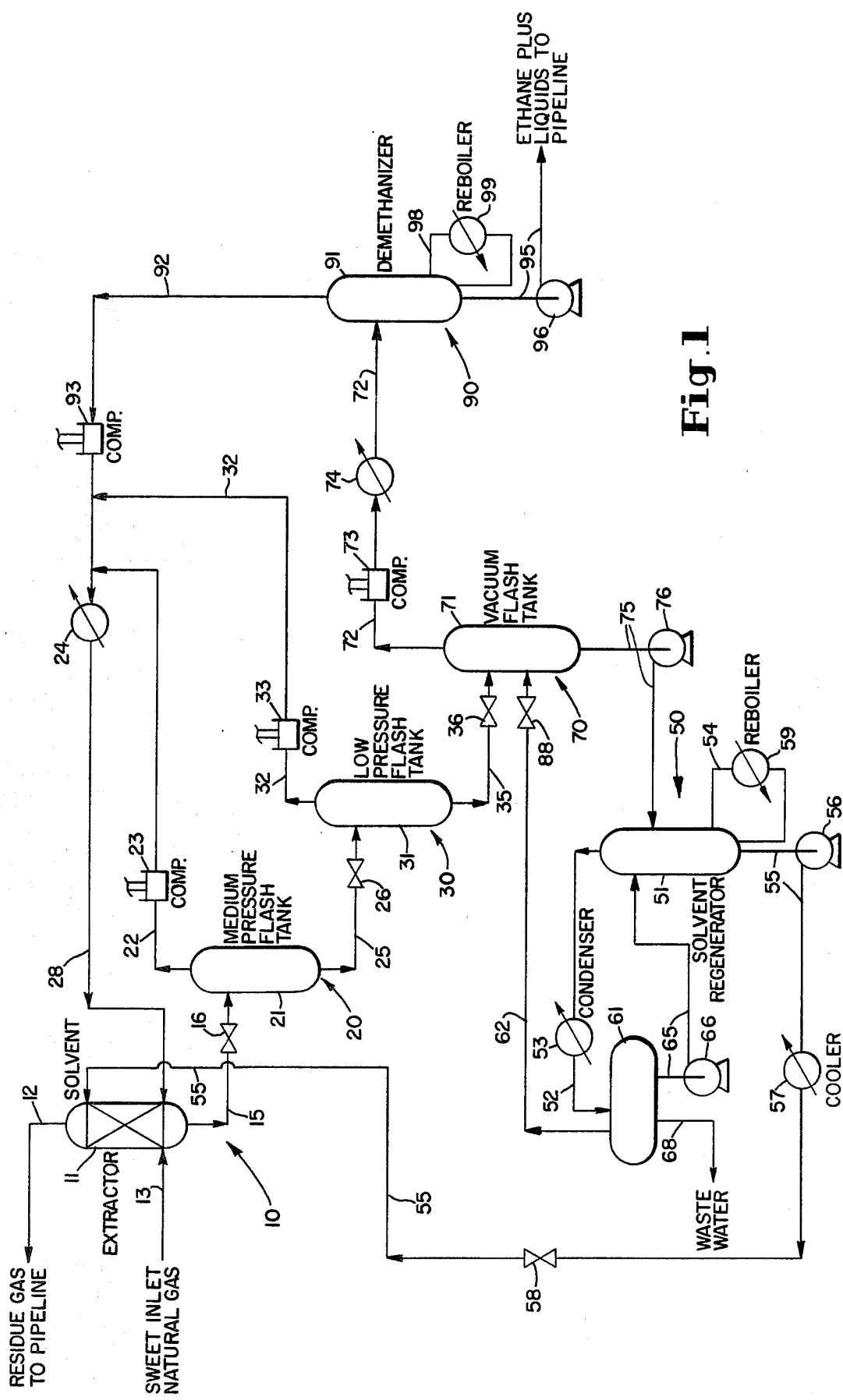
FIG. 1 is a schematic flow sheet for extraction of a recycle stream and a sweet inlet natural gas stream at 300–1300 psig with dimethyl ether of polyethylene glycol (DMPEG), and recovery of liquefied $C_2+$ hydrocarbons by using three flashing stages and a demethanizer.

Referring to FIG. 1, sweet natural gas at 300–1300 psig is introduced through line 13 into extractor 11 which may be any suitable tower filled with packing or containing perforated plates or bubble plates. Solvent enters through line 55 near the top of extractor 11, and residue gas is discharged through line 12 to the pipeline at 300–1300 psig. The rich solvent in line 15 contains water, methane, and other hydrocarbon components heavier than $CH_4$. The solvent in line 55 is a normally liquid dialkyl ether of a polyalkylene glycol, preferably polyethylene glycol dimethyl ether having 3 to 10 ethylene units and a molecular weight of 146 to 476, which is substantially dehydrated for maximum dehydration capacity.

Extractor 11 is maintained at about 20°–120° F., preferably 70°–80° F. Solvent is fed through line 55 at a rate sufficient to reduce the water content of the sweet natural gas to less than 12 pounds per million standard cubic feet and preferably to less than 7 pounds per million standard cubic feet. Under these conditions, the ethane and other hydrocarbon components of greater molecular weight in line 12 are reduced to a very low value. By altering the amount of solvent entering through line 55, the proportion of ethane to the predominant methane may be varied at will, but the solvent ratio is usually at 0.005 to 0.5 gallon of solvent per standard cubic foot of sweet natural gas.

The rich solvent in line 15 passes through valve 16, enters medium pressure flash tank 21 from which primarily methane and some heavier hydrocarbons are discharged through line 22 and is compressed by compressor 23. A mixture of solvent, hydrocarbon components, and water is discharged through line 25 and valve 26 and enters low pressure flash tank 31 from which a mixture of additional methane and some heavier hydrocarbons is discharged through line 32 and compressed by compressor 33. A mixture of solvent, remaining methane, ethane, and heavier hydrocarbons, and water is discharged through line 35 and valve 36, to vacuum flash tank 71 from which substantially all of the remaining hydrocarbons are discharged through line 72, compressed by compressor 73, cooled by condenser 74, and fed to demethanizer 91. A mixture of solvent, water and trace quantities of hydrocarbons is discharged from vacuum flash tank 71 through line 75, pumped by pump 76, and sent to solvent regenerator 51.

Solvent regenerator 51 is illustrated as utilizing a reboiler 59 which heats solvent, from the bottom of regenerator 51 and passing through line 54, in order to supply heat to the regenerator. The vaporized mixture of trace hydrocarbons, water, and solvent passes from the top of regenerator 51 through line 52, is condensed in condenser 53, and enters settler 61 from which solvent is discharged through line 65 and pump 66 to return to regenerator 51 as reflux. Waste water is discharged through line 68. The hydrocarbon vapors from Settler 61 leaves through line 62, is let down in pressure through valve 70, and enters vacuum flash tank 71. Water-free solvent is discharged from regenerator 51 through line 55 and pump 56, cooled in cooler 57 and returned to enter extractor 11.

The mixture of methane, ethane, propane, and heavier hydrocarbons in line 72 passes through compressor 73 and condenser/cooler 74 to demethanizer 91. Methane leaves demethanizer 91 through line 92, is compressed to a pressure slightly higher than pipeline pressure by compressor 93, is joined by the compressed mixture in line 32 and by the compressed methane with some heavier hydrocarbons in line 22, is cooled by heat exchanger 24, and passes through line 28 to enter extractor 11, thereby recycling the methane-rich recovered gas through the extractor.

Figure 2:
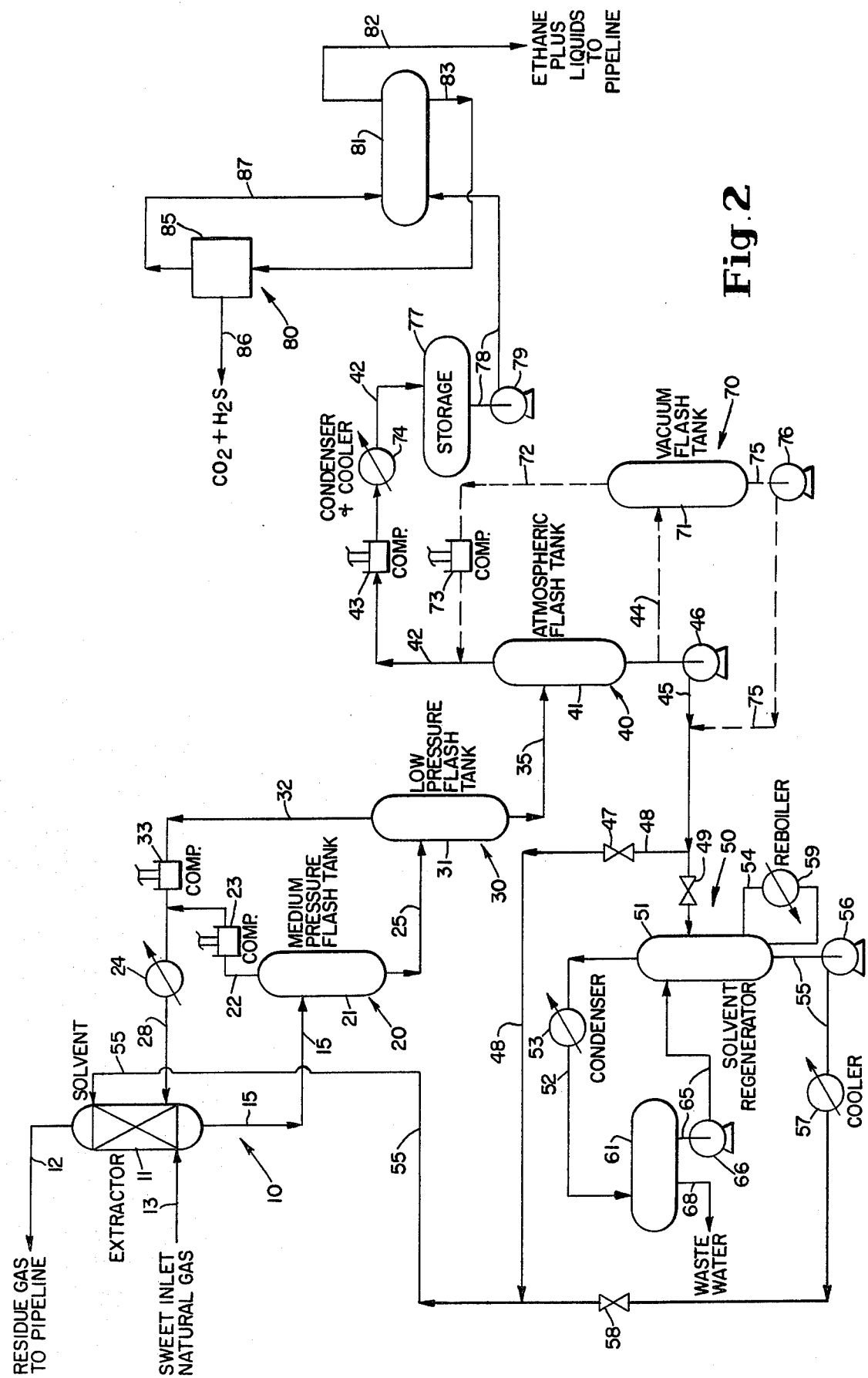
FIG. 2 is a schematic flow sheet for extraction with DMPEG of a recycle stream and a sour inlet natural gas stream at 300–1300 psig and recovery of $C_2+$ hydrocarbons by using four flashing stages, if necessary, with flashed products from the last two stages compressed, condensed and stored in a storage tank. The liquid hydrocarbons containing acid gas components are treated in a tail end unit using amines.

FIG. 2 relates to processing a sour natural gas which is received at the same range of pressure as the sweet natural gas treated according to the process of FIG. 1. As seen in the schematic flow sheet of FIG. 2, extractor 11, medium pressure flash tank 21, low pressure flash tank 31, solvent regenerator 51, and overhead column accumulator 61 are combined exactly as in FIG. 1 and are utilized for the same purposes.

However, the solvent stream in line 35 from low pressure flash tank 31 enters atmospheric flash tank 41, producing an overhead gas stream passing through line 42, compressor 43, and condensor/cooler 74 to enter storage tank 77.

If the inlet natural gas in line 13 is relatively lean or has trace quantities of $C_5+$ hydrocarbons, the solvent discharge from tank 41 moves through line 45, pump 46, and valve 49 to enter solvent regenerator 51 where it is processed as described for FIG. 1. However, if the converse is true and the inlet gas is indeed high in $C_5+$ hydrocarbons, the bottoms from tank 41 moves through line 44 to enter vacuum flash tank 71. The overhead therefrom passes through line 72 and compressor 73 to join line 42. The bottoms from tank 71 pass through line 75 and pump 76 to join line 45.

From storage tank 77, the liquid $C_2+$ hydrocarbons containing acid components moves through line 78 and pump 79 to amines contactor 81 which produces a sweet product in line 82, consisting essentially of ethane plus heavier hydrocarbon liquids for pipeline shipment. The sour amines stream in line 83 is stripped in unit 85, producing a $CO_2$ and $H_2S$ leaving through line 86. The sweet amines stream returns to contactor 81 by line 87.

There is no known problem as such that exists during simultaneous removal of acid gases and heavier hydrocarbons. However, when simultaneously removing $H_2S$ and $CO_2$ with heavier hydrocarbons, the hydrocarbons recovered need some form of treatment before shipping as specification product. As discussed in U.S. Pat. No. 3,770,622 with respect to propylene carbonate, the $CO_2$ can be vented from a separator while the hydrocarbons heavier than propane remain in the separator as a liquid layer which can be decanted. When using DMPEG as the solvent, on the other hand, both $H_2S$ and $CO_2$ must be extracted because DMPEG is a "physical" solvent.

As described earlier, cryogenic turboexpander technology is used to obtain very high ethane recoveries. In order to carry out such extraction from inlet gas streams containing high amounts of $CO_2$ (greater than 0.75 MOL%), it is very important to remove $CO_2$ from the gas stream before subjecting it to cryogenic temperatures in order to avoid $CO_2$ freeze-up problems in the equipment. Also it is more desirable to remove acid gases in liquid phase than in gaseous phase due to savings of capital and operating costs.

With the process of this invention, it is possible to remove ethane plus hydrocarbons from a relatively rich $CO_2$ stream without freezing problems and to remove $CO_2$ from desirable liquids in the liquid phase by using known amines.

As taught, for example, in U.S. Pat. No. 4,070,165, suitable sweetening amines are monoethanolamine (MEA), diethanolamine (DEA), diisopropanolamine (DIPA), and diglycolamine (DGA). Although it is common practice to utilize amines in an aqueous solution ranging from 15% to 70% by weight, it is preferred to utilize another solvent, such as methanol or acetone, for forming the amine solution circulated in amine unit 80 of this invention.

Other known sweetening processes which are suitable for treating the $C_2+$ products in storage tank 77 are also satisfactory. Particularly suitable processes are those which utilize solid-dessicant dehydration with such materials as activated alumina, silica gel, silica-alumina beads, and molecular sieves.

Figure 3:
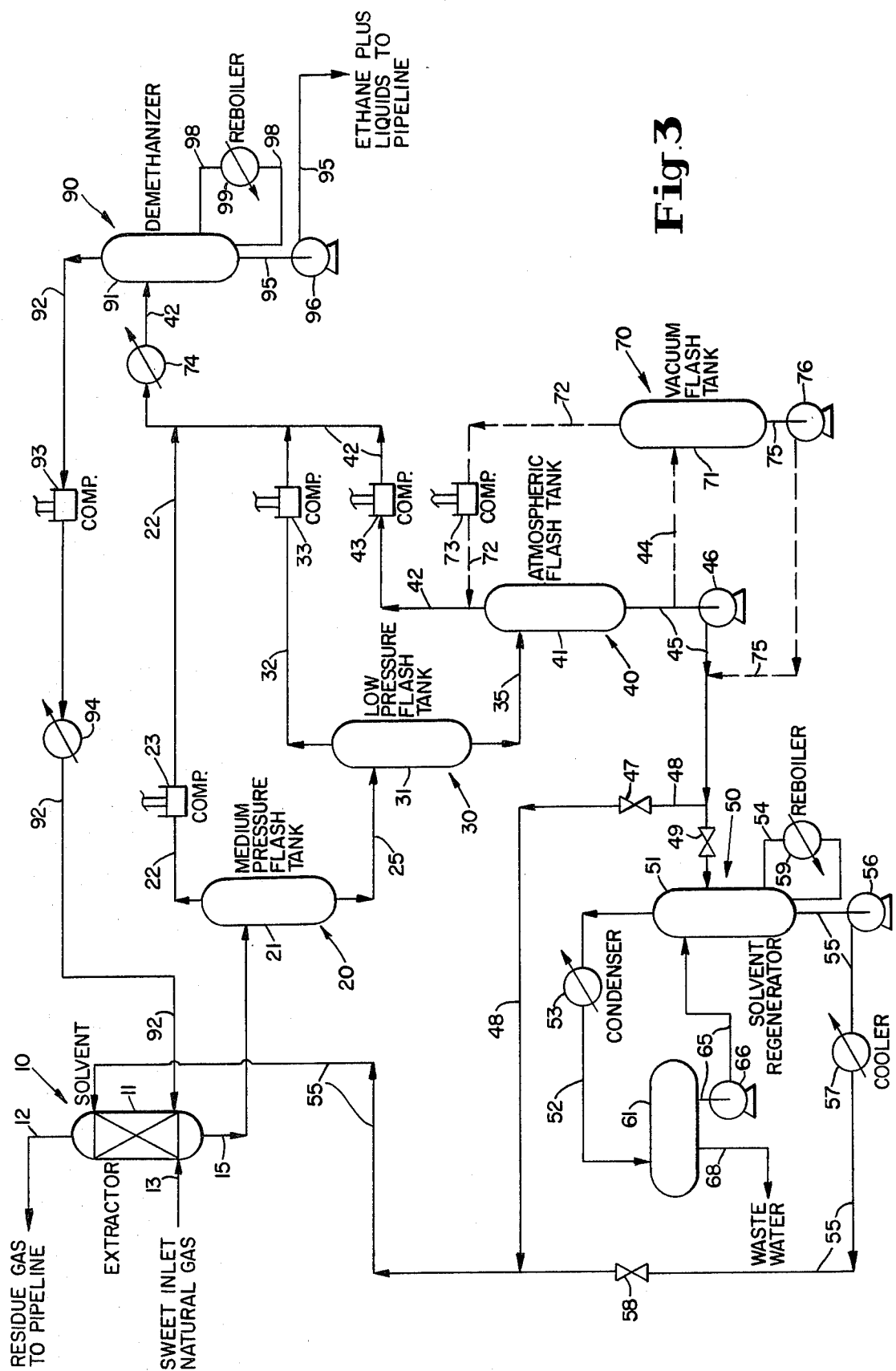
FIG. 3 is a flow sheet which is exactly the same as FIG. 1 except that there are four flashing stages, if necessary, and that all of the flashed products being fed to the demethanizer and only the overhead of the demethanizer is recycled directly to the extractor.

The process shown schematically in the flow sheet of FIG. 3 is directed to treating sweet inlet natural gas at 300–1300 psig and is very close to that of FIG. 1 in that it comprises a medium pressure flash unit 20, a low pressure flash unit 30, a vacuum flash unit 70, and a demethanizer unit 90. However, it additionally comprises an atmospheric flash unit 40, as in FIG. 2.

Unlike either FIG. 1 or FIG. 2, moreover, overhead discharge line 22 and overhead discharge line 32 join overhead discharge line 42, which is previously joined by overhead vacuum discharge line 72 (if unit 70 is utilized), so that all products from units 20,30,40, and 70 enter demethanizer unit 90. Demethanizer 91 and reboiler 99 must be larger, in consequence, than in the process of FIG. 1 for the same inlet quantity of sweet natural gas entering through line 13. On the other hand, all products of units 20,30,40, and 70 are treated alike, and very small quantities of heavier hydrocarbons are retained by the gas leaving in line 12.

The off gases from demethanizer 91 leaves through overhead discharge lines 92, is brought up to pipeline pressure in compressor 93, cooled in condenser 94, and returned to the lower portions of extractor 11.

Figure 4:
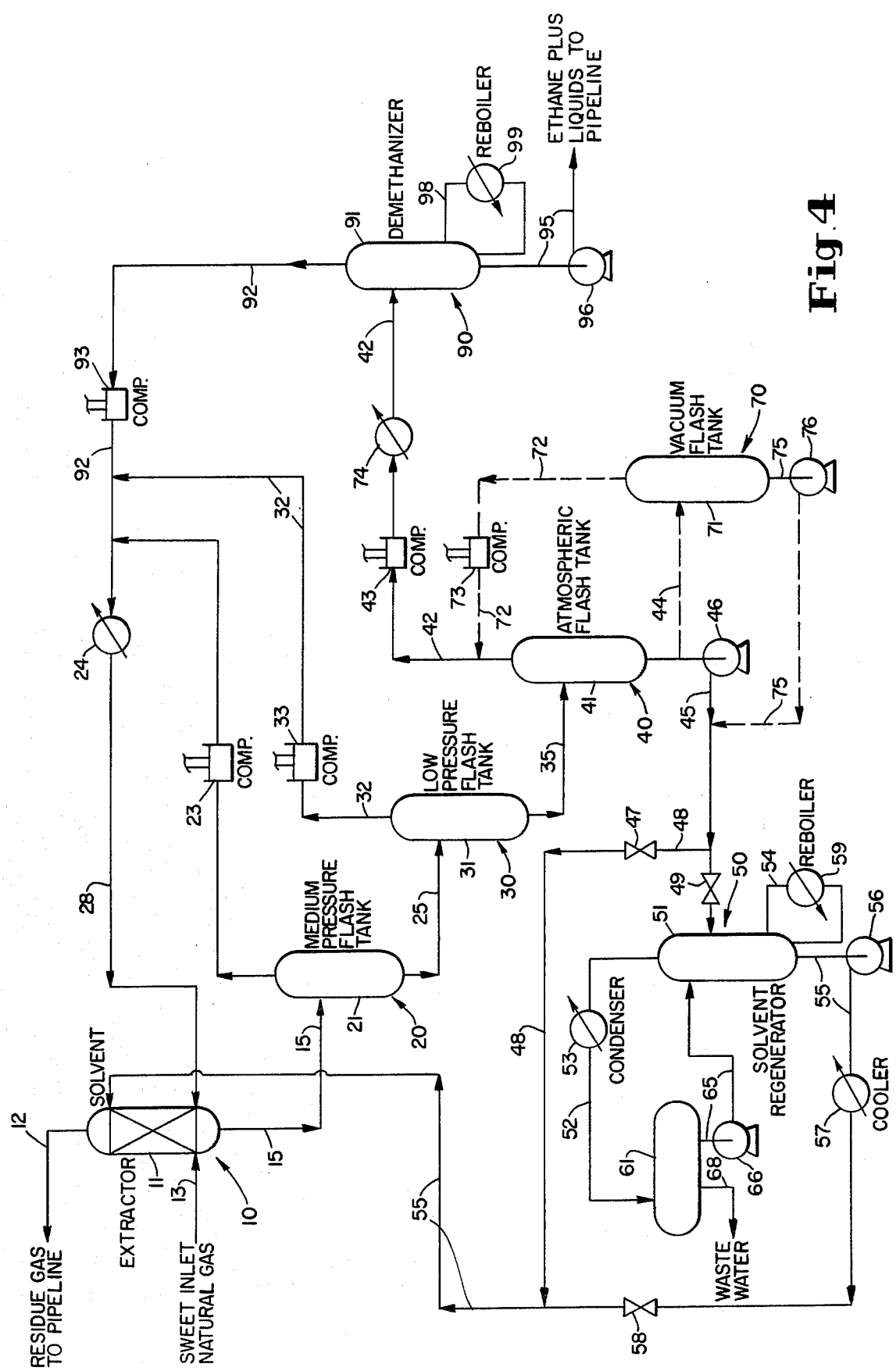
FIG. 4 is a flow sheet which is exactly the same as FIG. 3 except that the flashed products of the first two stages bypass the demethanizer and are recycled directly to the extractor.

The process shown schematically in the flow sheet of FIG. 4 is directed to treating sweet inlet natural gas at 300-1300 psig which enters extractor 11 through line 13. The process includes extractor unit 10, medium pressure flash unit 20, low pressure flash unit 30, atmospheric pressure flash unit 40, vacuum flash unit 70, solvent regenerator unit 50, and demethanizer unit 90, so that it is exactly like the process of FIG. 3 except that discharge lines 22 and 32 join discharge line 92 for cooling of all compressed products in condenser 24 and return to extractor 11 in combined line 28.

EXAMPLE

An ethane recovery plant, utilizing the process of FIG. 1, is designed and put into operation to treat one million standard cubic feet per day (1 MMSCFD) of dry sweetened natural gas for 95% ethane recovery. The composition of the natural gas entering extractor 11 of extractor unit 10 is as follows:

| Component | MOL % |
|---|---|
| Nitrogen | 2.02 |
| Methane | 80.62 |
| Ethane | 9.69 |
| Propane | 4.83 |
| ISO-Butane | 0.50 |
| N—Butane | 1.45 |
| ISO-Pentane | 0.30 |
| N—Pentane | 0.37 |
| Hexane Plus | 0.22 |
|  | 100.00 |
| Water Content 169 lbs/MMSCF dry gas | |
| Inlet Pressure 625 psia | |
| Inlet Temperature 120° F. | |

Sweetened natural gas stream 13 enters extractor 11 near its bottom. A recycle stream 28 also enters the extractor near the bottom. The combined gases from streams 13 and 28 flow upward in the extractor where they are contacted by lean solvent stream 55 flowing downwards. The molar ratio of solvent to fresh feed stream 13 is of the order of 1.36. Ethane and heavier liquids present in the inlet gas stream are selectively absorbed and removed from the extractor by stream 15. The remaining natural gas leaves the extractor through stream 12 which is primarily composed of nitrogen, methane, and small amounts of ethane, depending upon the desirable recoveries of ethane. Virtually all of the propane and heavier components are removed from stream 13. Stream 15 contains about 2.1 times as many moles of methane as moles of ethane.

In order to remove methane from recovered hydrocarbons while conserving energy consumption, the pressure of stream 15 is let down from 625 psia to 400 psia in medium pressure flash tank 21 where vapor stream 22, rich in methane (about 88 MOL% methane), is separated from liquid stream 25 which contains about 30% less methane, with about 94% of ethane present in stream 15. Stream 22 is compressed from 400 psia to 630 psia for recycle back to the extractor via stream 28.

In order to further reduce the amount of methane with ethane, the liquid pressure is reduced from 400 psia to 300 psia in low pressure flash tank 31. Here stream 32, consisting of about 86 MOL% methane, is separated from liquid stream 35 which contains about 1.19 moles of methane per mole of ethane and has about 51% less methane than the amount of methane present in stream 15. Vapors leaving via stream 32 are compressed to 630 psia for recycle to extractor 11 via stream 28.

In order to separate all hydrocarbon components from the solvent, the pressure of liquid stream 35 is reduced from 300 psia to 5 psia in a vacuum flash tank 71. The hydrocarbon vapors leaving tank 71 via stream 72 are compressed to 400 psia in compressor 73 and cooled to 20° F. in condensor 74 to condense ethane plus heavier hydrocarbons as product. While condensing the heavier hydrocarbons, some methane also gets condensed and is stripped by demethanizer 91. The demethanized product meeting specifications leaves the process via stream 95. The stripped methane from stream 72 leaves demethanizer 91 via stream 92 and is compressed to 630 psia for recycle to extractor 11 via stream 28. The combined streams 22, 32 and 92 are cooled to about 120° F. and recycled to extractor 11 via stream 28.

Depending upon the ethane recovery requirements, it may or may not be necessary to recycle stream 28 to the extractor. Instead, stream 28 could bypass the extractor and leave the plant by joining stream 12. The amount of methane that is present in stream 15 depends upon the partial pressures of desirable hydrocarbon components in stream 13.

Liquid stream 75 leaving vacuum flash tank 71 contains about 1.5 MOL% hydrocarbons and water, with the rest being the solvent. This stream is pumped into solvent regenerator 51 where contained water and hydrocarbons are separated overhead. The solvent regenerator operates typically at about 20 psia. The solvent is heated to about 300° F. to completely remove water from the solvent in the solvent regenerator and is cooled to about 120° F. before returning it to the extractor via stream 55. The water content of solvent stream 55 can be as high as 2 MOL% without any detrimental effect on the performance of the extractor, which would leave the temperature to which the solvent must be heated by reboiler 59.

The water is separated from the hydrocarbon vapors in column overhead accumulator 61 and leaves the process through stream 68. The hydrocarbon vapors are recycled under its pressure via stream 62 to vacuum flash tank 71.

The operation of the process as depicted in FIG. 1 can be more clearly understood by study of the compositions of the various streams in pound-mols per hour (LB-MOLS/HR). Eleven components of 15 streams are given in the following two tables.

TABLE I

MATERIAL BALANCE FOR ILLUSTRATIVE EXAMPLE

| Stream No. Components, Lb-Mols/Hr | 13 | 55 | 12 | 15 | 28 | 22 | 25 |
|---|---|---|---|---|---|---|---|
| Nitrogen | 2.22 | — | 2.22 | 0.11 | 0.11 | 0.07 | 0.04 |
| Methane | 88.48 | — | 88.26 | 25.76 | 25.54 | 7.69 | 18.07 |
| Ethane | 10.63 | — | 0.54 | 12.09 | 2.00 | 0.75 | 11.34 |
| Propane | 5.30 | — | Trace | 5.60 | 0.30 | 0.15 | 5.45 |
| ISO-Butane | 0.55 | — | — | 0.57 | 0.02 | 0.01 | 0.56 |
| N—Butane | 1.59 | — | — | 1.63 | 0.04 | 0.02 | 1.61 |
| ISO-Pentane | 0.33 | — | — | 0.33 | — | — | 0.33 |
| N—Pentane | 0.41 | — | — | 0.41 | — | — | 0.41 |
| Hexane Plus | 0.29 | — | — | 0.29 | — | — | 0.29 |
| Water | 0.39 | — | — | 0.39 | — | — | 0.39 |

TABLE I-continued

MATERIAL BALANCE FOR ILLUSTRATIVE EXAMPLE

| Stream No. Components, Lb-Mols/Hr | 13 | 55 | 12 | 15 | 28 | 22 | 25 |
|---|---|---|---|---|---|---|---|
| Solvent | — | 150.0 | — | 150.00 | — | — | 150.00 |
| TOTAL, LB-MOLS/HR | 110.19 | 150.00 | 91.02 | 197.18 | 28.01 | 8.69 | 188.49 |

TABLE II

MATERIAL BALANCE FOR ILLUSTRATIVE EXAMPLE

| Stream No. Components, Lb-mols/Hr | 32 | 35 | 72 | 75 | 92 | 95 | 68 | 62 |
|---|---|---|---|---|---|---|---|---|
| Nitrogen | 0.02 | 0.02 | — | — | 0.02 | — | — | — |
| Methane | 5.39 | 12.68 | 12.68 | 0.09 | 12.46 | 0.22 | — | 0.09 |
| Ethane | 0.71 | 10.63 | 10.63 | 0.44 | 0.54 | 10.09 | — | 0.44 |
| Propane | 0.15 | 5.30 | 5.30 | 0.51 | Trace | 5.30 | — | 0.51 |
| ISO-Butane | 0.01 | 0.55 | 0.55 | 0.09 | — | 0.55 | — | 0.09 |
| N—Butane | 0.02 | 1.59 | 1.59 | 0.31 | — | 1.59 | — | 0.31 |
| ISO-Pentane | — | 0.33 | 0.33 | 0.10 | — | 0.33 | — | 0.10 |
| N—Pentane | — | 0.41 | 0.41 | 0.15 | — | 0.41 | — | 0.15 |
| Hexane Plus | — | 0.29 | 0.29 | 0.13 | — | 0.29 | — | 0.13 |
| Water | — | 0.39 | — | 0.39 | — | — | 0.39 | Trace |
| Solvent | — | 150.00 | — | 150.00 | — | — | Trace | — |
| TOTAL, LB-MOLS/HR | 6.30 | 182.19 | 31.78 | 152.21 | 13.02 | 18.78 | 0.39 | 1.82 |

It is apparent from these tables that about 30% of the 25.76 pound-mols/hr of methane that is dissolved in solvent stream 15 is returned to extractor 11 in stream 22, about 21% is returned in stream 32, and about 48% is returned in stream 92. With respect to the 12.09 pound-mols/hr of ethane that leave in solvent stream 15, about 6.2% is returned to extractor 11 in stream 22, 5.9% is returned in stream 32, 4.5% is returned in stream 92, and 83.4% leaves in product stream 95. With respect to the 5.60 pound-mols/hr of propane in stream 15, 2.7% returns in stream 22, 2.7% returns in stream 32, and 94.6% is in product stream 95.

Without employing demethanizer unit 90, as in FIG. 2, it is clear that about half of the methane can become part of the product stream in line 82. Nonetheless, economic considerations, based upon product specifications, may easily obviate a need for demethanizer unit 90. Moreover, other design considerations may be important. For example, if the proportion of $C_2+$ hydrocarbons is unusually high, the amount of methane absorbed in the solvent is proportionately less.

What is claimed is:

1. A continuous process for separating water and hydrocarbons heavier than methane from a natural gas stream at pipeline pressures, comprising removing said water and said hydrocarbons heavier than methane as a $C_1+$ mixture to substantially any selected degree, including the following steps:

A. extracting said natural gas by flowing countercurrently to the natural gas stream a solvent consisting essentially of polyalkylene glycol dialkyl ethers at said pipeline pressures and at a rate sufficient to produce rich solvent containing water, methane, ethane, and hydrocarbons heavier than ethane, and residue natural gas of pipeline quality;
   B. returning said residue natural gas to a pipeline and flashing said rich solvent at a medium pressure to produce a $C_1$-rich gas fraction and a medium-pressure liquid mixture of said water, said solvent, and a $C_1+$ mixture of hydrocarbons;
   C. flashing said medium-pressure liquid mixture at low pressure to produce a $C_1$-rich gas fraction having a lower methane content than said gas fraction of step B and a low-pressure liquid mixture of said water, said solvent, and a $C_2+$ mixture of hydrocarbons containing minor amounts of methane;
   D. flashing said low-pressure liquid mixture at a pressure of up to approximately atmospheric pressure to produce a gas mixture of essentially all $C_1+$ hydrocarbons, and an atmospheric-pressure liquid mixture of said water, said solvent, and minor amounts of hydrocarbons;
   E. regenerating said solvent solely by removing said water and said minor amounts of hydrocarbons from said atmospheric pressure liquid mixture and returning the regenerated solvent to said extracting and returning said minor amounts of hydrocarbons to step D;
   F. compressing and cooling said $C_1$-rich gas fractions produced in step B and step C and returning said cooled gas fractions to said extracting in step A; and
   G. compressing, condensing, and cooling said gas mixture from step D to produce a liquid product.

2. The process of claim 1, wherein said residue natural gas contains less than 7 pounds of water vapor per million standard cubic feet as said selected degree.

3. The process of claim 2, wherein said regenerating is done by distillation.

4. The process of claim 3, wherein said regenerating is done by supplying heat to a reboiler to produce an overhead vaporous stream which is cooled, settled, pumped, and returned to said regenerating of step E after disposing of waste water therefrom.

5. The process of claim 4, wherein said approximately atmospheric pressure is up to about 25 psia, depending upon the content of hydrocarbons heavier than pentane in said natural gas stream.

6. The process of claim 5, wherein a D-1 step follows said step D and comprises flashing said atmospheric-pressure liquid mixture at a pressure less than said approximately atmospheric pressure and down to about 2 psia to produce a $C_1+$ gas mixture and a liquid mixture which is sent to said step E for said regenerating.

7. The process of claim 6, wherein said gas mixtures from said step D and from step D-1 are sent to a demethanizing step in which methane is removed and then compressed, cooled, and sent to said extracting in said step A and in which ethane plus liquids is produced as a liquid product.

8. The process of claim 7, wherein said $C_1$-rich gas fractions from steps B and C are compressed and cooled, as in step F, and are then additionally passed to said demethanizing step before said returning of said methane content thereof to said extracting in step A.

9. The process of claims 6 or 7, wherein said methane content from said demethanizing step bypasses said extracting step to join said residue natural gas in step B.

10. The process of any one of claims 1 through 9 wherein the solvent is a mixture containing not less than 20% by volume alkyl ether of polyethylene glycol and no more than 80% by volume of alkyl ether of polypropylene glycol.

11. The process of claim 1, wherein a step C-1 follows step C, replacing step D, and comprises flashing said low-pressure liquid mixture at a pressure less than approximately atmospheric pressure and down to about 2 psia to produce a $C_1+$ gas mixture and a liquid mixture which is sent to said step E for said regenerating.

12. The process of claim 11, wherein said $C_1+$ gas mixture is compressed, cooled, and sent to a demethanizing step in which methane is removed and then compressed, cooled, and sent to said extracting in said step A, producing ethane plus liquids as liquid product from said demethanizing step.

13. The process of any one of claims 1 through 12, wherein said natural gas stream is a sweet natural gas.

14. The process of any of one claims 1 through 12, wherein said natural gas stream is a sour natural gas.

15. The process of claim 14, wherein said liquid products of claims 1, 7, and 12 are treated in a sweetening step wherein at least $CO_2$ and $H_2S$ are removed.

16. The process of claim 15, wherein said sweetening step comprises contacting said product with an amine stream.

17. The process of claims 1, 7, or 12, wherein said removing said hydrocarbons heavier than methane to said subsantially any selected degree is achieved by altering the flow rate of said solvent in said step A.

18. The process of claim 17, wherein said solvent flow rate ranges from 0.005 to 0.5 gallon of solvent per standard cubic foot of natural gas stream.

19. The process of claim 18, wherein the ratio of methane to ethane in said liquid product of said step G is varied at will by said altering of said flow rate.

20. The process of claim 19, wherein said varying the ratio of methane to ethane results in removing up to approximately 2% of said ethane and recovering at least 98% of propane and all heavier hydrocarbons as said liquid product.

21. The process of claim 20, wherein the inlet gas pressure for said natural gas stream ranges from 300 psig to 1300 psig and from an ambient temperature of 80° F. to 120° F.

22. The process of claim 21, wherein said polyalkylene glycol dialkyl ethers have a range of molecular weight from 146 to 476, containing 3–10 ethylene units.

23. The process of claim 22, wherein said glycol comprises polypropylene glycol.

24. The process of claim 23, wherein said solvent is a mixture of dimethyl ethers of polyethylene and polypropylene glycol.

25. The process of claim 24, wherein said mixture consists of a minimum of 20% by volume of dialkyl ether or polyethylene glycol and a maximum of 80% by volume of dialkyl ether of polypropylene glycol.

* * * * *